(12) United States Patent
Komachi et al.

(10) Patent No.: US 7,184,142 B2
(45) Date of Patent: Feb. 27, 2007

(54) RAMAN PROBE AND RAMAN SPECTRUM MEASURING APPARATUS UTILIZING THE SAME

(75) Inventors: Yuichi Komachi, Tokyo (JP); Hideo Tashiro, Saitama (JP); Hidetoshi Sato, Saitama (JP); Katsuo Aizawa, Kanagawa (JP)

(73) Assignees: Riken, Saitama (JP); Machida Endoscope Co., Ltd., Tokyo (JP)

( * ) Notice: Subject to any disclaimer, the term of this patent is extended or adjusted under 35 U.S.C. 154(b) by 317 days.

(21) Appl. No.: 10/807,328

(22) Filed: Mar. 24, 2004

(65) Prior Publication Data

US 2006/0146322 A1 Jul. 6, 2006

(30) Foreign Application Priority Data

Mar. 25, 2003 (JP) .............................. 2003-083480

(51) Int. Cl.
*G01J 3/44* (2006.01)
*G01N 21/65* (2006.01)

(52) U.S. Cl. ..................................... 356/301
(58) Field of Classification Search ................. 356/301
See application file for complete search history.

(56) References Cited

U.S. PATENT DOCUMENTS

| | | | | |
|---|---|---|---|---|
| 3,906,241 A | * | 9/1975 | Thompson | 356/301 |
| 5,351,117 A | * | 9/1994 | Stewart et al. | 356/301 |
| 6,370,406 B1 | * | 4/2002 | Wach et al. | 356/301 |
| 2003/0191398 A1 | * | 10/2003 | Motz et al. | 600/478 |
| 2004/0073120 A1 | * | 4/2004 | Motz et al. | 600/478 |

* cited by examiner

*Primary Examiner*—F. L. Evans
(74) *Attorney, Agent, or Firm*—Sughrue Mion, PLLC

(57) ABSTRACT

A Raman probe for measuring Raman spectrum includes an exciting-end light guiding path for guiding excitation light from a light source to a sample; a receiving light-guide path for guiding a light signal from said sample to a detector; a band-pass filter for passing said excitation light and blocking Raman-scattered light produced from said exciting-end light guiding path; a pipe for securing said band-pass filter inside said pipe, said pipe being mounted on a light-outgoing end of said exciting-end light guiding path; and an edge filter mounted on a light-incident end of said receiving light-guide path, said edge filter passing Raman-scattered light from said sample while blocking the excitation light. The edge filter is a short-wavelength transmitting filter that permits passage of wavelengths shorter than the excitation wavelength.

6 Claims, 5 Drawing Sheets

RAMAN PROBE AND RAMAN SPECTRUM MEASURING APPARATUS UTILIZING THE SAME

BACKGROUND OF THE INVENTION (1) Technical Field

The present invention relates to a Raman probe connecting an excitation light source, a Raman spectrograph and a sample, and a Raman spectrum measuring apparatus utilizing the Raman probe.

(2) Background Art

In recent years, there is a growing need for the development of non-invasive medical diagnostic techniques that are more objective and more quantitative. As a result, high expectations are placed on spectroscopic technologies, for example in connection with the diagnosis and treatment of arterial sclerosis. A vascular endoscope has recently been developed for the diagnosis of arterial sclerosis. This endoscope, however, is only capable of observing the color and form of an affected part, and it is not suitable for quantitative observation or definite diagnosis of the progress of the symptom. In the nidus of sclerosis, various lipids, such as cholesterol ester, are accumulated, and it is expected that the progress of arterial sclerosis can be diagnosed by analyzing the amount of accumulated lipids and the ratio of components. For this diagnosis, Raman spectroscopic analysis has been proposed as a highly objective definite diagnosing method. Based on the determination of the fingerprint region of lipids and the CH rolling vibration mode (~3000 cm$^{-1}$), the ratio of cholesterol to the entire amount of lipids can be analyzed. Expectations are placed on diagnosis based on spectrum analysis using a Raman scattering measuring extra-fine fiber probe that is capable of being introduced into blood vessels.

When measuring Raman scattering of a sample in situ, for example, excitation light is guided by means of a Raman probe to a measured portion of the sample, and signal light from the sample is guided via the probe to a Raman spectrograph. However, optical fibers, such as a quartz fiber, that are used as the Raman probe themselves generate Raman scattered light. Raman scattered light is also generated by the optical fiber on the exciting end as well as one on the receiving end. Raman scattered light from the excitation-side optical fiber is shone onto the sample together with the excitation light, and as it enters the receiving optical fiber, it interferes with the Raman scattered light generated from the sample. Further, if the excitation light with which the sample has been irradiated is reflected or scattered by the sample and is then incident on the receiving optical fiber, Raman scattering is caused in the receiving optical fiber as a result, which would also interfere with the measuring of the Raman scattered light generated from the sample.

These interfering light not only lower the S/N of the measurement signal, but could even make it impossible to perform measurement if the signal from the sample is very weak. Thus, the Raman scattering caused by the optical fiber in the Raman probe must be eliminated. For that purpose, it is known to deposit a thin film on the edge surface of the optical fiber by evaporation to thereby form an interference filter. To the tip of the exciting fiber, a band-pass filter is secured with an adhesive in order to eliminate the Raman scattered light generated from the excitation-light transmitting quartz fiber (see Non-patent Document 3).

[Patent Document 1] JP Patent Publication (Kokai) No. 11-218445 A (1999)

[Patent Document 2] U.S. Pat. No. 5,842,995

[Non-patent Document 1] Appl. Spec. 6,619, 1999

SUMMARY OF THE INVENTION

In order to form an interference filter on the edge surface of an optical fiber, evaporation is carried out for each optical fiber. It is difficult, however, to form a film with a uniform thickness on a minute region by evaporation. Yield significantly decreases if the diameter of the optical fiber that is used is reduced to 0.2 mm or smaller, and it is difficult to obtain a plurality of fibers with identical performance that are necessary for a single probe assembly. The evaporation technique is also disadvantageous in that individual fibers must eventually be coupled (see Appl. Spec. 6,619, 1999), which would inevitably lead to coupling losses. Furthermore, while there is no problem as long as a continuous-oscillation laser is used as the light source, if a pulsed laser is used that has a high peak-power intensity, the adhesive with which the band-pass filter is secured can be burned and carbonized by the energy of laser, thereby blocking light. Thus, it has been impossible to employ high-output lasers as the light source.

In view of the foregoing problems of the prior art, it is an object of the invention to provide a Raman probe that can be used with high-intensity excitation light without producing light that interferes with the measurement of Raman spectrum. It is another object of the invention to provide a Raman spectrum measuring apparatus capable of conducting a Raman spectrum measurement accurately on a sample located at a distance.

In accordance with the invention, when a filter is provided at the tip of the fiber, a receiving-end filter is doughnut- or ring-shaped, with an exciting-end filter disposed at the center. A light-blocking structure is provided between the exciting-end filter and the receiving-end filter such that the exciting-end and the receiving-end are completely separated. Because the front surface of the incident-end or outgoing-end of the fiber is a filter surface, there is no coupling loss that could result when one fiber is coupled to another. Further, on the receiving-end, a sole hard-coat filter with a diameter of less than 1 mm, which is prepared by a cutting process, is attached to a plurality of optical fibers, such that the problems of the thickness of the optical fiber or yield in the evaporation method can be overcome.

DESCRIPTION OF THE PREFERRED EMBODIMENTS OF THE INVENTION

The invention will be hereafter described with reference to the drawings.

Figure 1:
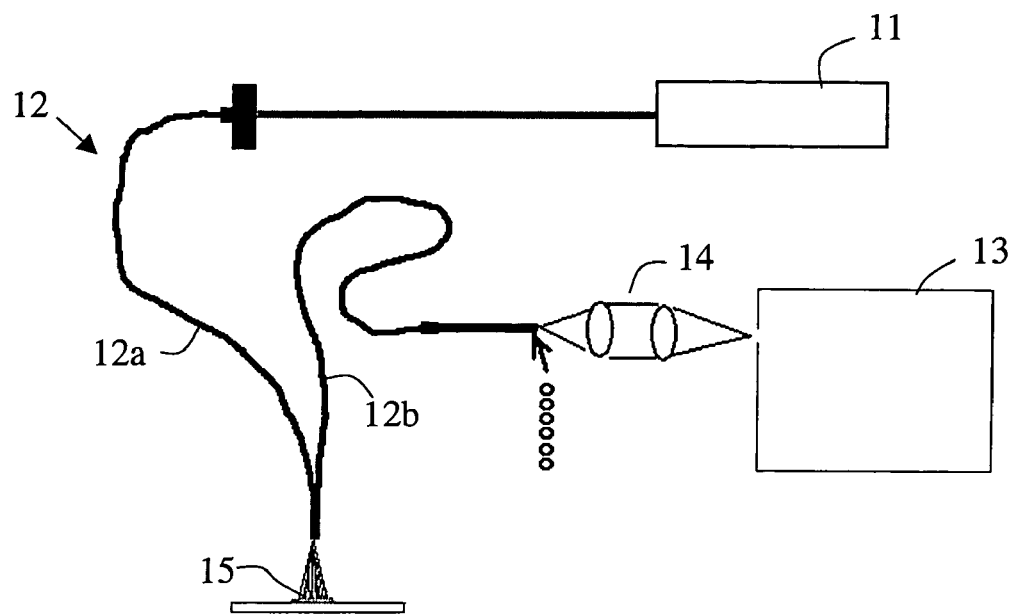
FIG. 1 schematically shows a Raman spectrum measuring apparatus utilizing a Raman probe according to the invention.

FIG. 1 schematically shows a Raman spectrum measuring apparatus utilizing a Raman probe according to the invention.

This Raman spectrum measuring apparatus comprises a laser light source 11 as the excitation light source, a Raman spectrograph 13, and a Raman probe 12 connecting between the excitation light source and a sample 15, and between the sample 15 and the Raman spectrograph 13. The Raman probe 12 comprises an exciting light-guide path 12a and a receiving light-guide path 12b. The exciting-end light guiding path is made up of a single quartz fiber, for example. The receiving light-guide path is made up of a plurality of quartz fibers, for example. In this case, the plural quartz fibers in the receiving light-guide path are arranged in a circle around the exciting quartz fiber on a light-incident end towards the sample. On a light-outgoing end opposite an incident slit of the Raman spectrograph, the plural quartz fibers of the receiving light-guide path are arranged in a row corresponding to the shape of the incident slit. Thus, a line-shaped light beam emitted from the light-outgoing end of the receiving quartz fibers is incident on the incident slit of the Raman spectrograph 13 via optics 14.

Figure 2:
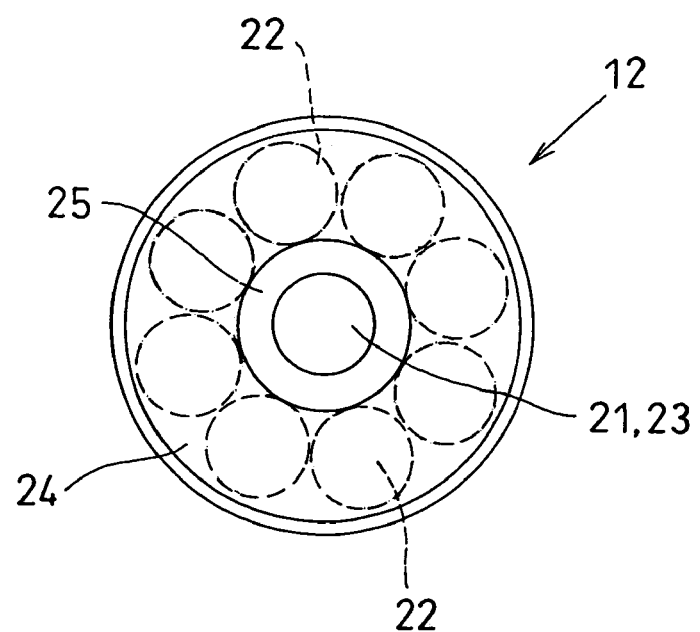
FIG. 2 shows an excitation-light outgoing end of an example of the Raman probe of the invention.

Hereafter an example of the structure of the Raman probe of the invention will be described. FIG. 2 shows the end surface of an example of the Raman probe on its excitation-light outgoing end.

As shown in FIG. 2, when the Raman probe 12 is seen from its excitation-light outgoing end, a single exciting-end optical fiber 21 is positioned at the center and is surrounded by 8 receiving optical fibers 22. To the tip of the exciting-end optical fiber 21, a band-pass filter 23 is attached, the filter only passing the excitation wavelength emitted by the laser light source 11. On the tip of the receiving optical fibers 22 an edge filter (long-wavelength transmitting filter) 24 is mounted, the filter blocking the excitation wavelength while allowing the Raman-scattered light coming from the sample to pass. A stainless-steel pipe 25 is mounted on the tip of the exciting-end optical fiber 21, whereby the passing of light between the exciting-end optical fiber 21 and the receiving optical fibers 22 is blocked. As a result, the excitation light emitted by the exciting-end optical fiber 21 is prevented from directly entering the receiving optical fibers 22. When the anti-Stokes line with shorter wavelengths than the excitation light is to be measured as Raman-scattered light, the edge filter may be provided by a short-wavelength transmitting filter that blocks the excitation wavelength while permitting the passage of wavelengths shorter than the excitation wavelength.

Figure 3:
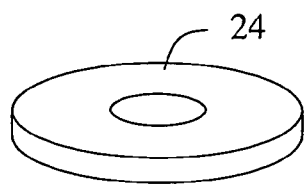
FIGS. 3(a) and 3(b) schematically show an edge filter mounted on the tip of a receiving optical fiber, and a cross-section of an exciting-end optical fiber on the tip of which a band-pass filter is mounted.
Figure 3:
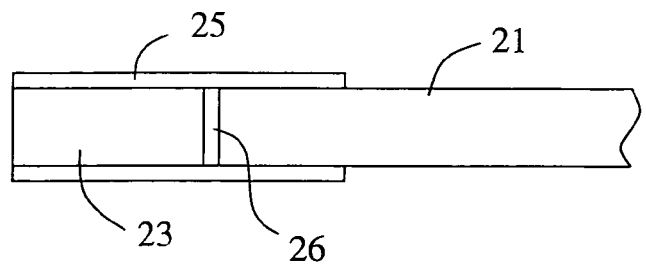

FIGS. 3(a) and 3(b) schematically show the edge filter 24 mounted on the tip of the receiving optical fibers 22, and a cross-section of the exciting-end optical fiber 21 on which the band-pass filter 23 is mounted.

The edge filter 24 mounted on the tip of the receiving optical fibers 22 has a circular shape with an opening formed at the center, as shown, in FIG. 3(a). In one example, when a quartz fiber with a diameter of 125 μm was used for the exciting-end optical fiber 21 and receiving optical fibers 22, the diameter of the edge filter 24 was set to be 500 μm and its thickness was set to be 100 μm. The diameter of the opening at the center, through which the excitation light was to be passed, was 200 μm.

In the preparation of the edge filter, an interference filter with desired characteristics was prepared by performing a vacuum evaporation on a glass substrate. The filter was cut into pieces several millimeters square and was then subjected to precision polishing down to a thickness of 100 μm. An opening with a diameter of 200 μm was then formed at the center of the thus polished filter, and the external diameter of the filter was finally adjusted to 500 μm about the opening.

As shown in FIG. 3(b), at the tip of the exciting-end optical fiber 21, a band-pass filter 23 is mounted, the band-pass filter 23 being inserted into an opaque pipe 25. The band-pass filter 23 was prepared by forming an interference filter on the glass substrate by vacuum deposition and then grinding the filter by precision polishing down to the diameter of the fiber required. While FIG. 3(b) shows an air gap 26 between the band-pass filter 23 and the tip surface of the exciting-end optical fiber 21, the air gap 26 may be eliminated so that the band-pass filter 23 is disposed in contact with the tip surface of the exciting-end optical fiber 21.

The band-pass filter 23 was mounted on the tip of the exciting-end optical fiber 21 in the following manner. Initially, the pipe 25 was mounted on the tip of the exciting-end optical fiber 21 and fixed thereon, and then the band-pass filter 23 was secured to the pipe 25. Care was taken not to allow the adhesive to enter where laser light passes. The internal diameter of the pipe 25 was substantially the same as the diameter of the exciting-end optical fiber 21. The pipe 25 should preferably be made of metal, such as stainless steel. The glass substrate on which the interference filter was formed was inserted into the pipe 25 so that the interference filter was opposite the exciting-end optical fiber 21.

Figure 4:
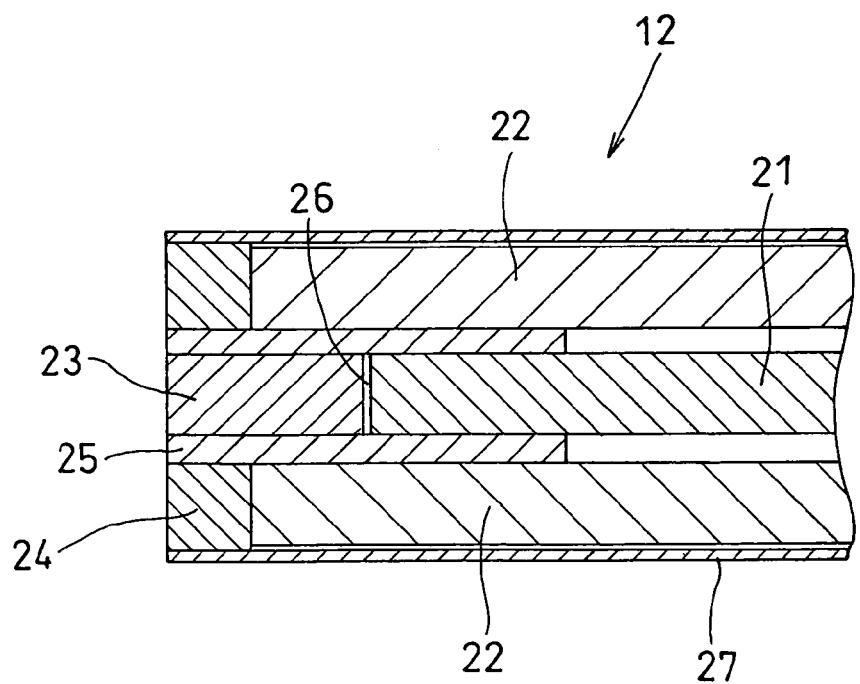
FIG. 4 is a cross section of an excitation-light outgoing end of the Raman probe in which the band-pass filter and the edge filter are incorporated.

FIG. 4 is a cross-section of the excitation-light outgoing end of the Raman probe 12 in which the band-pass filter 23 and edge filter 24 are incorporated. Both band-pass filter 23 and edge filter 24 are disposed so that their surfaces on which the interference filter is formed are opposite the exciting-end optical fiber 21 and the receiving optical fibers 22, respectively. The edge filter 24 is bonded to the tip of the receiving optical fibers 22 with an adhesive, such as glass resin. The sides of the tip are covered with an external covering 27 made of a stainless-steel pipe or a resin film.

Because it is preferable that the Raman probe 12 has a small diameter, the wall thickness of the pipe 25 mounted at the tip of the exciting-end optical fiber 21 was set to be several tens of a micrometer such as, for example, 35 μm, as discussed below. In the illustrated example, a stainless-steel pipe 25 with an external diameter of 200 μm and an internal diameter of 130 μm was used. Forming the pipe with plastics or polyimides, for example, is not desirable, as it would lead not only to the generation of fluorescence or Raman scattering due to excitation light, but also to the leakage of light to the receiving optical fibers 22, which would cause crosstalk. While in the illustrated examples the exciting-end optical fiber 21 and the receiving optical fibers 22 employ optical fibers with the same diameter, the diameter of the sole exciting-end optical fiber 21 may be made larger than the diameter of the receiving optical fibers 22. A plurality of exciting-end optical fibers 21 may be provided and bundled before being inserted into the pipe 25. The number of the receiving optical fibers 22 may be larger or smaller than 8; however, if the light-receiving solid angle is to be increased in order to improve measurement sensitivity, it is preferable to closely pack the receiving optical fibers 22 around the pipe 25 such that there is no gap between the adjacent receiving optical fibers 22.

By adopting such a filter mount structure, not only the performance of the Raman probe can be significantly enhanced but also its manufacture can be made easier, so that high-quality Raman probes can be produced in large quantities. As there is no adhesive between the exciting-end optical fiber and the band-pass filter, the weatherability can be significantly improved over the structures utilizing adhesives, which allows the use of a high-power excitation laser light. By using the Raman probe with the above-described structure, Raman scattering was measured without any problems even when a high-power pulsed laser with 50 W output was introduced.

Hereafter, an example of measurement using the Raman probe of the invention will be described. As the excitation light source, a pulse-oscillating titan sapphire laser was used. The excitation wavelength was 720 nm, and the measured sample was calcium carbonate. The pulse-oscillating titan sapphire laser was a variable wavelength laser. During Raman spectrum measurement, there could be produced fluorescence depending on the wavelength of excitation light that interferes with Raman scattering. It is therefore necessary to select a wavelength that does not cause fluorescence, and the pulse-oscillating titan sapphire laser is a most appropriate light source in this sense.

Figure 5:
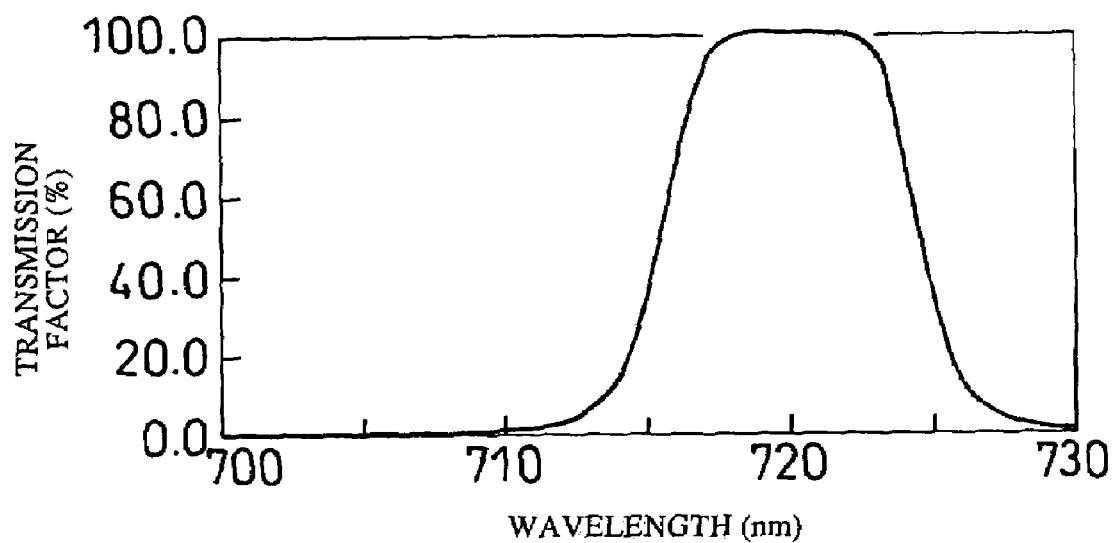
FIGS. 5(a) and 5(b) show the characteristics of the filters mounted at the tip of the Raman probe.
Figure 5:
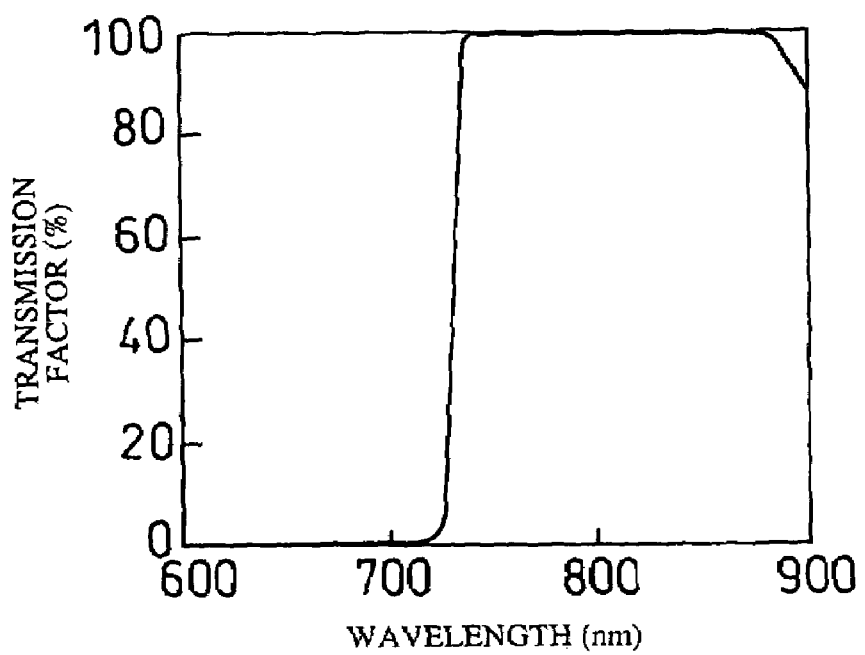

FIGS. 5(a) and 5(b) show the characteristics of the filter mounted on the tip of the Raman probe in the example. FIG. 5(a) shows the transmission characteristics of the band-pass filter 23 mounted on the exciting-end optical fiber 21 where the transmission center wavelength is 720 nm and the half-width value is 10 nm. FIG. 5(b) shows the transmission characteristics of the edge filter 24 mounted on the receiving optical fibers 22, where the optical density ("OD") value is 3 or more at 720 nm.

Figure 6:
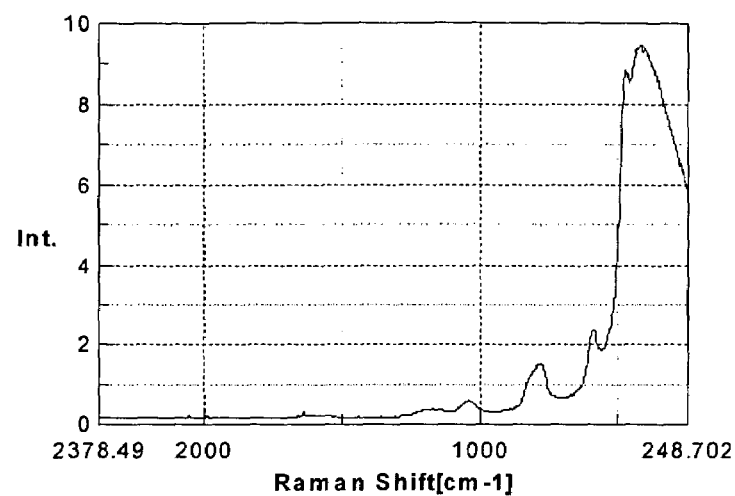
FIG. 6 shows the Raman spectrum of a quartz fiber.

FIG. 6 shows the Raman spectrum of a quartz fiber. There is Raman scattering from the quartz and Raman scattering from the materials added to the fiber. As will be seen from the chart, a relatively broad spectrum is obtained.

Figure 7:
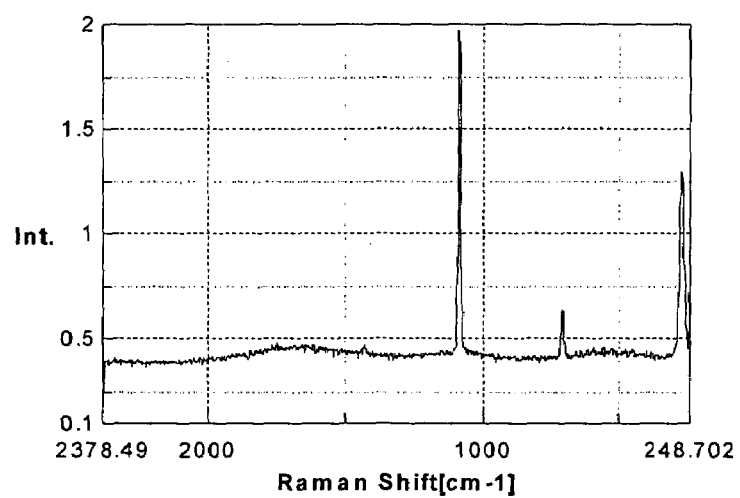
FIG. 7 shows the Raman spectrum of calcium carbonate.

FIG. 7 shows the Raman spectrum of calcium carbonate. The spectrum was obtained by directly irradiating calcium carbonate with laser light and analyzing the reflected light using a spectroscope. No fiber was used in the optical paths.

Figure 8:
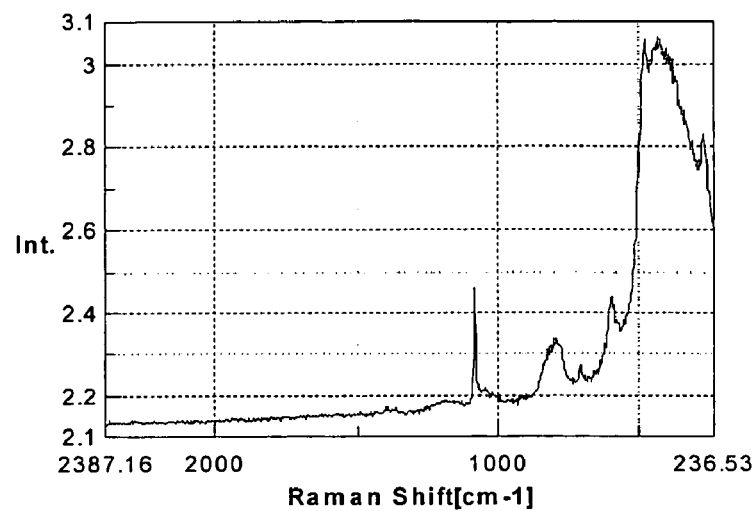
FIG. 8 shows the Raman spectrum of calcium carbonate measured with the Raman probe in which quartz fibers with no filters were incorporated.

FIG. 8 shows the Raman spectrum of calcium carbonate that was measured using a Raman probe in which quartz fibers without filters were incorporated. When a quartz fiber probe is used for the measurement, excitation light passes through the quartz fiber, so that the sample is irradiated with light in which excitation light and Raman scattering from the quartz fiber are mixed. While Raman scattering is produced from calcium carbonate, excitation light is also reflected and scattered by the sample surface. Both of them are incident on the receiving fiber. The excitation light that is incident on the receiving fiber produces Raman scattering again in the receiving optical fiber. As a result, the sum of these components is detected in the spectrum. Thus, the observed spectrum comprises the Raman scattering spectrum of the quartz fiber as shown in FIG. 6 on which the Raman scattering spectrum of calcium carbonate shown in FIG. 7 is superposed.

Figure 9:
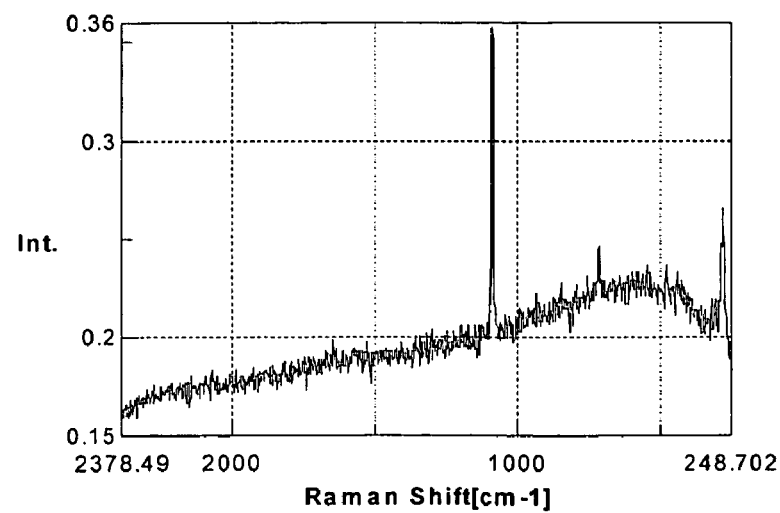
FIG. 9 shows the Raman spectrum of calcium carbonate measured with the Raman probe of the invention.

FIG. 9 shows the Raman-scattering spectrum of calcium carbonate measured using the Raman probe 12 of the invention. As described above, Raman scattering is generated from the quartz fibers, for both the exciting-end optical fiber 21 and the receiving optical fibers 22. In the Raman probe 12 of the invention, this excess Raman scattering is eliminated. Specifically, a band-pass filter 23 is mounted at the tip of the exciting-end optical fiber 21 to eliminate Raman scattering generated in the fiber, and the excitation light that attempts to enter the receiving optical fibers 22 is eliminated by an edge filter 24 mounted on the receiving-end. By the operation of these filters, a substantially identical spectrum to that of FIG. 7 can be obtained even when optical fibers are used.

In accordance with the invention, a Raman probe can be obtained that can be used with high-intensity excitation light without producing light that interferes with the measurement of Raman scattering. By employing the Raman probe, a highly accurate Raman scattering measurement can be made.

What is claimed is:

1. A Raman probe for measuring Raman spectrum, comprising:
   an exciting-end light guiding path for guiding excitation light from a light source to a sample;
   a receiving light-guide path for guiding a light signal from said sample to a detector;
   a band-pass filter for passing said excitation light and blocking Raman-scattered light produced from said exciting-end light guiding path;
   a pipe for securing said band-pass filter inside said pipe, said pipe being mounted on a light-outgoing end of said exciting-end light guiding path; and
   an edge filter mounted on a light-incident end of said receiving light-guide path, said edge filter passing Raman-scattered light from said sample while blocking the excitation light;
   wherein the edge filter is a short-wavelength transmitting filter that permits passage of wavelengths shorter than the excitation wavelength.

2. The Raman probe according to claim 1, wherein said receiving light-guide path is made up of a plurality of optical fibers the light-incident ends of which are arranged around said pipe,
   wherein said edge filter is formed in a circular shape with an opening provided at the center, and
   wherein the tip of said pipe is inserted into said opening.

3. The Raman probe according to claim 1, wherein said pipe is made of metal.

4. The Raman probe according to claim 1, wherein said exciting-end light guiding path consists of a single optical fiber.

5. A Raman-spectrum measuring apparatus, comprising:
   a laser light source;
   a spectroscope; and
   a Raman probe for guiding light emitted by said laser light source to a sample and for guiding Raman-scattered light from said sample to said spectroscope;
   wherein the Raman probe is one according to claim 1.

6. The Raman-spectrum measuring apparatus according to claim 5, wherein said laser light source is a pulsed light source.

* * * * *